United States Patent [19]

Valcke

[11] Patent Number: 5,223,524
[45] Date of Patent: Jun. 29, 1993

US005223524A

[54] SYNERGISTIC COMPOSITIONS CONTAINING PROPICONAZOLE AND TEBUCONAZOLE

[75] Inventor: Alex R. A. Valcke, Wechelderzande, Belgium

[73] Assignee: Janssen Pharmaceutica N.V., Beerse, Belgium

[21] Appl. No.: 861,703

[22] Filed: Apr. 1, 1992

Related U.S. Application Data

[63] Continuation of Ser. No. 496,727, Mar. 21, 1990, abandoned.

[30] Foreign Application Priority Data

Apr. 19, 1989 [GB] United Kingdom ................ 8908794

[51] Int. Cl.$^5$ ............................................. A01N 43/64
[52] U.S. Cl. .................................................... 514/383

[58] Field of Search ........................................ 514/383

[56] References Cited

FOREIGN PATENT DOCUMENTS 0052424 5/1982 European Pat. Off. .

Primary Examiner—Allen J. Robinson
Attorney, Agent, or Firm—Charles J. Metz

[57] ABSTRACT

Synergistic antifungal compositions containing tebuconazole and propiconazole for treating plants or the loci thereof, or for use in wood-preservation or protection of biodegradable materials. Method of treating plants comprising the administration of tebuconazole and propiconazole. Method of protecting wood, wood-products and biodegradable materials from fungal attack and destruction.

4 Claims, No Drawings

SYNERGISTIC COMPOSITIONS CONTAINING PROPICONAZOLE AND TEBUCONAZOLE

This is a continuation of application Ser. No. 496,727, filed Mar. 21, 1990, now abandoned.

BACKGROUND OF THE INVENTION

Various classes of compounds are known as antimicrobial and in particular antifungal compounds. Among these classes, the group of imidazole and triazole derivatives is of particular interest and several such compounds are now widely used as antimicrobials and in particular as antifungals.

Further, there are known fungicidal combinations comprising two or more such fungicidally active compounds, from e.g. EP-A-0,237,764.

It now has been found that the fungicidal compounds propiconazole and tebuconazole act synergistically.

DESCRIPTION OF THE INVENTION

The present invention is concerned with synergistic mixtures or compositions containing an antifungally effective amount of the compound tebuconazole or a salt form thereof and propiconazole, a salt, a stereoisomer or a stereoisomeric mixture thereof.

Propiconazole as mentioned hereinabove is the generic name of the compound 1-[[2-(2,4-dichlorophenyl)-4-propyl-1,3-dioxolan-2-yl]methyl]-1H-1,2,4-triazole, which compound may be represented by the formula

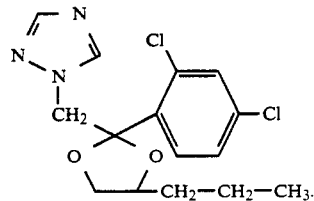

(I)

This compound, its synthesis as well as its antifungal properties are described in U.S. Pat. No. 4,079,062, incorporated herein by reference.

Tebuconazole as mentioned hereinabove is the generic name of the compound α-[2-(4-chlorophenyl)ethyl]-α-(1,1-dimethylethyl)-1H-1,2,4-triazol-1-ethanol, which compound may be represented by the formula

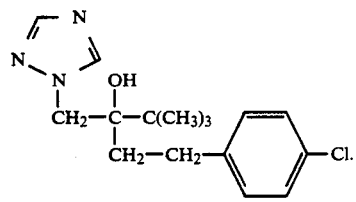

(II)

This compound, its synthesis as well as its antifungal properties are described in EP-A-0,040,345 and EP-A-0,052,424.

The active ingredients for use in the mixtures or compositions according to the present invention may be used as stereochemical mixtures or as pure stereoisomers. In particular, propiconazole may occur as 2,4-cis or 2,4-trans isomers. The 2,4-cis isomer is preferably used in the compositions of the present invention. Or use may be made of stereochemical mixtures containing predominantly (over 50%) the cis isomer.

The active ingredients (I) and (II) may be present in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid and the like; or organic acids, such as, for example, acetic, propanoic, hydroxyacetic, 2-oxopropanoic, 2-hydroxypropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term salt form also comprises metal complexes which the basic components (I) or (II) may form. One of the components may occur as a complex and the other not; or both components may occur as a complex. Metal complexes as mentioned above consist of a complex formed between one or more molecules of the active ingredient and one or more organic or inorganic metal salts. Examples of said organic or inorganic metal salts comprise the halogenides, nitrates, sulfates, phosphates, acetates, trifluoroacetates, trichloroacetates, propionates, tartrates, sulfonates, e.g. methanesulfonates, 4-methylbenzenesulfonates, salicylates, benzoates and the like, of the metals of the second main group of the periodical system, e.g. the magnesium or calcium salts, of the third or fourth main group, e.g. aluminum, tin, lead and the like metals, as well as metals of the first to the eighth transition groups of the periodical system such as, for example, chromium, manganese, iron, cobalt, nickel, copper, zinc and the like. Preferred are the metals pertaining to the transition elements of the fourth period. The metals may be present in any of their possible valences. The complexes can be mono- or polynuclear and may contain one or more parts of the organic molecule as ligands.

The term salt as used hereinabove also comprises the solvates which the compounds propiconazole and tebuconazole are able to form. Examples of such solvates are e.g., the hydrates, alcoholates and the like.

The synergistic mixtures according to the present invention are most useful to combat fungi or prevent the growth thereof in plants or the loci thereof; particularly in plant products, including wood; in pulpwood for paper manufacture; and also in biodegradable materials such as, for example, textiles of natural fibers, e.g. cotton, flax, hemp, wool, silk and the like; textiles of synthetic fibers, e.g. polyamide, polyacrylonitrile or polyester fibers, or of mixtures of such fibers; coatings, e.g. oil paints, dispersion paints, lacquers, lacquer films, whitewash, finishing stains and the like; glues and other such materials which are biodegradable by fungi.

The synergistic mixtures of the present invention are active against a broad range of fungi. As examples of such fungi there may be named Ascomycetes (e.g. Venturia, Podosphaera, Erysiphe, Monilinia, Uncinula, Aureobasidium, Sclerophoma); Basidiomycetes (e.g. Hemileia, Rhizoctonia, Puccinia, Coniophora, Serpula, Poria, Uromyces, Gloeophyllum, Lentinus, Coriolus, Irpex); Fungi imperfecti (e.g. Botrytis, Helminthosporium, Rhynchosporium, Fusarium, Septoria, Cercospora, Alternaria, Pyricularia, Penicillium, Geotrichum).

The synergistic mixtures according to the present invention possess advantageous curative, preventive and systemic fungicidal activity to protect plants, in particular culture plants. The present mixtures can be used to protect plants or parts of plants, e.g. fruits, blossoms, flowers, foliage, stems, roots, tubers of plants or culture plants infected, harmed or destroyed by micro-organisms, whereby later-growing parts of plants are protected against such micro-organisms. They can further be used in seed disinfection (fruits, tubers, cereal grains), to treat plant cuttings as well as to combat phytopathogenous fungi occurring in the soil. The mixtures of the present invention are particularly attractive due to their good plant tolerance and lack of environmental problems.

As examples of the wide variety of culture plants in which the combination of active ingredients according to the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees suc as conifers. This enumeration of culture plants is given with the purpose of illustrating the invention and not of delimiting it thereto.

A particular mode of administering a synergistic composition containing the active ingredients (I) and (II), is the administration to the aboveground parts of plants, in particular to the leaves thereof (leaf-application). The number of applications and the administered doses are chosen in accordance with the biological and climatic conditions of life of the causative agent. The active ingredients though, can also be applied to the soil and get into the plants through the root system (systemic activity), in case the locus of the plants is sprayed with a liquid composition or if the compounds are added to the soil in a solid formulation e.g. in the form of a granulate (soil application). The compounds (I) and (II) can also be coated on seeds, in case the seed grains seed are drenched consecutively with a liquid composition of the active ingredients or if they are coated with a previously combined composition.

The synergistic mixtures according to the present invention are also useful as wood-preserving agents, for example against wood-destroying or wood-discoloring fungi. As wood which can be preserved with the synergistic compositions according to the present invention is considered, for example, wood products such as timber, lumber, railway sleepers, telephone poles, fences, wood coverings, wicker-work, windows and doors, plywood, particle board, waferboards, chipboard, joinery, bridges or wood products which are generally used in house-building, construction and carpentry.

Wood which is preserved from staining, discoloring and decay is meant to be protected from for example, moulding, rotting, loss of its useful mechanical properties such as breaking strength, resistance to shock and shearing strength, or decrease of its optical or other useful properties due to the occurrence of odour, staining and spot formation. These phenomena are caused by a number of micro-organisms of which the following are typical examples: *Aspergillus species, Penicillium species, Aureobasidium pullulans, Sclerophoma pityophilla, Verticillium species, Alternaria species, Rhizopus species, Mucor species, Paecilomyces species, Saccharomyces species, Trichoderma viride, Chaetomium globosum, Stachybotrys atra, Myrothecium verrucaria, Oospora lactis* and other staining and wood decay fungi. Special emphasis should be put on the good activity against moulds and staining fungi such as *Aureobasidium pullulans, Sclerophoma pityophilla, Aspergillus niger, Penicillium funiculosum, Trichoderma viride, Alternaria alternata,* decay and soft rot fungi such as *Chaetomium globosum, Trychophyton mentagrophytes, Coriolus versicolor, Coniophora puteana, Poria monticola, Merulius (Serpula) lacrymans* and *Gloeophyllum trabeum*, and yeasts such as *Candida albicans* and *Saccharomyces species*. Other susceptible fungi are, for example, *Penicillium glaucum, Paecilomyces variotii, Cladosporium herbarum, Ceratocystis species, Lentinus lepideus, Trametes versicolor* and *Stereum hirsutum*.

In order to protect wood from decay it is treated with synergistic compositions according to the present invention. Such treatment is applied by several different procedures such as, for example, by treating the wood in closed pressure- or vacuum systems, in thermal- or dip systems and the like, or by a wide variety of surface treatments, e.g. by brushing, dipping, spraying or soaking the wood with a formulation containing the wood-preserving agents propiconazole and tebuconazole.

Synergistic compositions according to the present invention can also advantageously be applied in the cellulose and paper industry, in particular to protect pulpwood for paper manufacture from fungal attack.

The amount of each of the active ingredients propiconazole (I) and tebuconazole (II) in the synergistic compositions according to the present invention is such that a synergistic antifungal effect is obtained upon application. In particular, it is contemplated that in the compositions to be used directly, the concentration of tebuconazole taken as base equivalent, may range from 10 to 15000 ppm, in particular from 50 to 12000 ppm or from 50 to 6000 ppm, more in particular from 100 to 3000 ppm; and the concentration of propiconazole taken as base equivalent is contemplated to range from 10 to 15000 ppm, in particular from 50 to 10000 ppm or from 100 to 8000 ppm, more in particular from 200 to 6000 ppm. In many instances said compositions to be used directly can be obtained from concentrates upon dilution with aqueous or organic media, such concentrates also being intended to be covered by the term composition as used in the definitions of the present invention. The content of the active ingredients in the above-indicated compositions is from 0.01 to 95%, preferably from 0.1 to 50% more preferably from 0.1 to 20% and in particular from 0.2 to 15% by weight. The compositions according to the invention are preferably used in the form of solutions.

The ratio between the active ingredients of formula (I) and (II) in said synergistic compositions may vary within relatively broad ranges and will be dependent on the application aimed at, however said ratio will be such that a synergistic fungicidal effect is obtained with both active ingredients. Particularly, it is contemplated that the weight ratio between the active ingredients (I) and (II) (propiconazole:tebuconazole) may be situated between 50:1 and 1:50, more particularly between 20:1 and 1:20. Preferably said ratio is between 10:1 and 1:10, more preferably between 5:1 and 1:5.

The active ingredients of formula (I) and (II) are used in unmodified form or together with adjuvants conventionally employed in the art of formulation. The formulations, i.e. the compositions, preparations or mixtures containing the active ingredients and, where appropriate, a solid or liquid adjuvant, are prepared following art-known procedures, e.g. by homogeneously mixing and/or grinding the active ingredients with extenders, e.g. solvents, solid carriers and, where appropriate, surface-active compounds (surfactants), to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, brushing, dipping, soaking or impregnating, are chosen in accordance with the intended objectives and the prevailing circumstances.

Appropriate carriers and adjuvants for use in the compositions of the present invention may be solid or liquid and correspond to suitable substances known in the art for preparing formulations for treating plants or the loci thereof, or for treating plant products, in particular for treating wood, such as, for example, natural or regenerated mineral substances, solvents, dispersants, surfactants, wetting agents, adhesives, thickeners, binders, fertilizers, anti-freeze agents and other active ingredients.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McClutcheon's Detergents and Emulsifiers Annual", MC Publishing Corp., Ridgewood, N.J., 1981; H.

Stache, "TensidTaschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

Particularly advantageous additives useful to improve the application and reduce the dose of the active ingredients, are the natural (animal or plant) or synthetic phospholipids of the cephalin or lecithin type such as, for example, phosphatidylethanolamine, phosphatidylserine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylcholine mixtures. Synthetic phospholipids are for instance, dioctanylphosphatidylcholine and dipalmitoylphosphatidylcholine.

In case of liquid formulations, and particularly of aqueous or alcoholic formulations, it is recommendable to add an appropriate surfactant, either from the anionic, cationic or neutral type. In particular said surfactants will be of the cationic type and more in particular said surfactant is a quaternary ammonium salt or a mixture of quaternary ammonium salts. Such quaternary ammonium surfactants comprise, for example, ammonium salts having four hydrocarbon radicals which may optionally be substituted with halo, phenyl, substituted phenyl or hydroxy; said hydrocarbon radicals in particular being alkyl or alkenyl radicals; they may also be derived from fatty acids or alcohols, e.g. cetyl, lauryl, palmityl, myristyl, oleyl and the like or from the hydrosylates form coconut oil, tallow oil, soy bean oil, or the hydrogenated forms thereof, and the like.

Examples of such quaternary ammonium salts are of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl alkyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

As used in the foregoing enumeration of quaternary ammonium salts, the terms "coco", "tallow" and "hydrogenated tallow" designate those hydrocarbon radicals derived from the hydrosylates of coconut oil, tallow oil or hydrogenated tallow oil. The weight ratio between said quaternary ammonium surfactants and the active ingredient (I) is situated between 1:1 and 10:1. Excellent results are obtained when said ratio is about 5:1.

Apart from both the aforementioned active ingredients of formula (I) and (II), the compositions according to the present invention may further contain other active ingredients, e.g. other microbiocides, in particular fungicides, and also insecticides, acaricides, nematicides, herbicides, plant growth regulators and fertilizers. As antimicrobial agents, which may be used in combination with the active substances there may be considered products of the following classes: phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydrodiphenylethers such as, for example, 2-hydroxy-3,2′4′-trichlorodiphenylether, phenylphenol, 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo- or trichlorocarbanilide, dichlorotrifluoromethyldiphenylurea; tribromosalicylanilide; 2-bromo-2-nitro-1,3-dihydroxypropane; dichlorobenzoxazolon; chlorohexidine; isothia- and benzisothiazolone derivatives.

As insecticidal agents which may be used in combination with the azoles of formula (I) the following classes of products may be considered: insecticides having a natural origin, e.g., nicotine, rotenone, pyrethrum and the like; chloridinated hydrocarbons, e.g., lindane, chlordane, endosulfan and the like; organic phosphor compounds, e.g., phoxim, chlorpyrifos, diazinon, parathion, dichlorovos, dimethoate and the like; carbamates, e.g., carbaryl, aldicarb, methiocarb, propoxur and the like; biological insecticides, e.g., products originating from *Bacillus thuringiensis*; synthetic pyrethroids, e.g., permethrin, allethrin, cypermethrin, deltamethrin, cyfluthrin, halothrin and the like.

In view of their solubility in organic solvents the active ingredients are well suited for application in non-aqueous media which is of interest in wood-preservation. The wood or wood products to be protected can easily be impregnated with such solutions. As organic solvents there may be used aliphatic and aromatic hydrocarbons, their chlorinated derivatives, acid amides, mineral oils, alcohols, ethers, glycolethers, such as, for example, methylene chloride, propylene glycol, methoxyethanol, ethoxyethanol, N,N-dimethylformamide and the like or mixtures of such solvents, to which there may be added dispersants (e.g., emulsifiers such as sulfurated ricinus oil, fatty alcohol sulfates etc.) and/or other additives.

Particularly attractive formulations comprise waterdilutable wood-preservative liquids containing an appropriate amount of a suitable solvent, a suitable solubilizer and both the active ingredients. Preferably there is used 10–80% of a solvent, 20–80% of a solubilizer and from 0.01 to 10% of the active ingredients (I) and (II).

Preferred solubilizers to be used in the said waterdilutable wood-preservative liquids are selected from:
i) addition products of 1 to 60 moles of ethylene oxide with 1 mole of a phenol which is further substituted with at least one $C_{1-15}$ alkyl group; and ii) addition products of 1 to 60 moles of ethylene oxide with 1 mole of ricinus oil.

The most preferred solubilizers are selected from:

i) addition products of 1 to 60 moles of ethylene oxide with 1 mole of nonylphenol or octylphenol; and ii) addition products of 1 to 60 moles of ethylene oxide with 1 mole of ricinus oil.

Said suitable solvent should fulfil the requirements of sufficiently solubilizing the active ingredients and, when combined with the solubilizer, of being homogeneously miscible with a predominantly aqueous medium. Preferred solvents are 2-butoxyethanol, butyl 2-hydroxyacetic acid ester and propyleneglycol monomethylether.

Said water-dilutable wood-preserving liquids have the advantage that almost instantaneously homogeneous or quasi homogeneous solutions are formed by mixing these liquids with predominantly aqueous media. These solutions have an extremely high physical stability, not only at ambient temperature, i.e. at temperatures comprised between 15° C. and 35° C., but also at decreased temperatures. Thus the physical stability of said solutions does not deteriorate after several freeze-thaw cycles. Said homogeneous solutions further unite the advantages of moistening the wood-surface well and penetrating the wood to a high degree, resulting in a high uptake of the solution and its active ingredients by the wood, and, consequently, obtaining the desired preservation of the treated wood. Additionally, due to a more uniform uptake of the aqueous solution the wood-preserving liquids and the resulting aqueous solutions are particularly useful in treatment techniques which require the possibility of a continuous process, such as, for example, impregnation- or dip techniques.

In addition, the solutions formed with the wood-preserving liquids unite in themselves the hereinabove mentioned advantages with those which are characteristic of predominantly aqueous media, such as, for example, a relatively high flashpoint and reduced toxicity, resulting in advantageous influence on the environment and the health and safety of the applicator, lack of irritation and the like benefits.

In the wood-preserving solutions which are used to be contacted with the wood, said solutions either being a composition as described hereinabove or prepared therefrom upon dilution with a suitable solvent, the concentration of the compound of formula (II) may vary between 100 and 10000 ppm, in particular between 200 and 5000 ppm and preferably between 500 and 1000 ppm; the concentration of the compound of formula (I) may vary between 100 and 15000 ppm, in particular between 300 and 7500 ppm and preferably between 750 and 1500 ppm.

In said wood-preserving solutions, the ratio between the active ingredients (I) and (II) (propiconazole:-tebuconazole) will be such that a synergistic fungicidal effect is obtained with both active ingredients. Particularly, the weight ratio between (I) and (II) may range from 20:1 to 1:2, more particularly from 10:1 to 1:1 and preferably will range from about 5:1 to about 1:1.

The synergistic mixtures or compositions to be used directly may also be obtained from separate compositions containing the active ingredients or from the technical active ingredients themselves, by mixing and/or diluting with aqueous or organic media and/or optionally further adding adjuvants such as those described hereinabove. Said separate compositions generally are such as described hereinbefore for compositions containing both active ingredients. Of particular interest to some users may be preparation of custom-made formulations from both active ingredients in unmodified, technical form, thus allowing maximal flexibility in the application of the present synergistic mixtures of propiconazole and tebuconazole.

In a further aspect of the present invention there is provided a method of combating fungi comprising treating plants or the loci thereof, or treating plant products such as wood; or pulpwood for paper manufacture, or treating biodegradable materials simultaneously, separately or sequentially with an effective amount of a synergistic, antifungal mixture or composition as described hereinabove.

In a further embodiment of the present invention there is provided a method of preserving wood, wood products and biodegradable materials from deterioration by fungi. This method comprises the application to or incorporation in said wood or wood products or in or to said biodegradable materials, of a synergistic mixture or composition as defined hereinabove.

The active ingredient of formula (I) and that of formula (II) can be applied to the plants or to the loci thereof or to plant products, such as wood or to biodegradable materials such as textiles, simultaneously, or can also be administered consecutively within a time period selected so that both active ingredients are allowed to act synergistically as antifungals, e.g. within 24 hours. In such applications, the active ingredients are used optionally together with adjuvants conventionally employed in the art of formulation such as carriers, surfactants or other useful additives. Therefore, the present invention also concerns products containing a compound of formula (I), propiconazole or a salt, a stereoisomer or a stereoisomeric mixture thereof, and a compound of formula (II), tebuconazole or a salt thereof, as a combination for simultaneous, separate or sequential use in antifungal applications. Such products may consists of a package comprising containers with both active ingredients, preferably in formulated form. Such formulated forms in general have the same composition as described for the formulations containing both active ingredients.

The following examples are intended to illustrate and not to limit the scope of the present invention in all its aspects. Unless otherwise stated all parts therein are by weight.

EXAMPLES

A) Composition Examples

Throughout all examples percentages are by weight.

EXAMPLE 1

Wettable powders

|  | a) | b) | c) |
| --- | --- | --- | --- |
| propiconazole | 10% | 25% | 0.25% |
| tebuconazole | 10% | 25% | 0.25% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredients were thoroughly mixed with the adjuvants and the mixture was thoroughly ground in a suitable mill, affording wettable powders which could be diluted with water to give suspensions of the desired concentration.

EXAMPLE 2

Emulsifiable concentrates

|  | a) | b) | c) | d) |
|---|---|---|---|---|
| propiconazole | 5% | 0.5% | 7% | 9% |
| tebuconazole | 5% | 0.5% | 3% | 1% |
| octylphenol polyethylene glycol ether (4-5 moles of ethylene oxide) | 3% | 3% | 3% | 3% |
| calcium dodecylbenzenesulfonate | 3% | 3% | 3% | 3% |
| castor oil polyglycol ether (36 moles of ethylene oxide) | 4% | 4% | 4% | 4% |
| cyclohexanone | 30% | 10% | 30% | 30% |
| dimethylbenzene mixture | 50% | 79% | 50% | 50% |

|  | e) | f) | g) | h) |
|---|---|---|---|---|
| propiconazole | 5% | 2.5% | 4% | 9% |
| tebuconazole | 5% | 2.5% | 1% | 1% |
| calcium dodecylbenzenesulfonate | 5% | 8% | 8% | 5% |
| castor oil polyethylene glycol ether (36 moles of ethylene oxide) | 5% | — | — | 5% |
| tributylphenol polyethylene glycol ether (30 moles of ethylene oxide) | — | 12% | 12% | — |
| cyclohexanone | — | 15% | 15% | — |
| dimethylbenzene mixture | 80% | 60% | 60% | 80% |

Emulsions of any required concentration could be obtained from these concentrates by dilution with water.

EXAMPLE 3

Dusts

|  | a) | b) | c) | d) |
|---|---|---|---|---|
| propiconazole | 0.05% | 0.5% | 0.075% | 0.095% |
| tebuconazole | 0.05% | 0.5% | 0.025% | 0.005% |
| talcum | 99.9% | — | 99.9% | 99.9% |
| kaolin | — | 99% | — | — |

Usable dusts were obtained by mixing the active ingredients with the carriers, and grinding the mixture in a suitable mill.

EXAMPLE 4

Extruder granulates

|  | a) | b) | c) | d) |
|---|---|---|---|---|
| propiconazole | 5% | 0.5% | 9.5% | 0.9% |
| tebuconazole | 5% | 0.5% | 0.5% | 0.1% |
| sodium lignosulfate | 2% | 2% | 2% | 2% |
| carboxymethylcellulose | 1% | 1% | 1% | 1% |
| kaolin | 87% | 96% | 87% | 96% |

The active ingredients were mixed and ground with the adjuvants, and the mixture was subsequently moistened with water. The mixture was extruded and dried in a stream of air.

|  | e) | f) | g) | h) |
|---|---|---|---|---|
| propiconazole | 2.5% | 5% | 4.5% | 8% |
| tebuconazole | 2.5% | 5% | 0.5% | 2% |
| kaolin | 94% | — | 94% | — |
| highly dispersed silicic acid | 1% | — | 1% | — |

|  | e) | f) | g) | h) |
|---|---|---|---|---|
| attapulgite | — | 90% | — | 90% |

The active ingredients were dissolved in dichloromethane, the solution was sprayed onto the carrier, and the solvent was subsequently evaporated off in vacuo.

EXAMPLE 5

Coated granulates

|  | a) | b) | c) |
|---|---|---|---|
| propiconazole | 1.5% | 4% | 9% |
| tebuconazole | 1.5% | 1% | 1% |
| polyethylene glycol (mol. wt. 200) | 2% | 2% | 2% |
| kaolin | 95% | 93% | 88% |

The active ingredients were uniformly applied, in a mixer, to the kaolin moistened with polyethylene glycol. Non-dusty coated granulates were obtained in this manner.

EXAMPLE 6

Suspension concentrates

|  | a) | b) | c) | d) |
|---|---|---|---|---|
| propiconazole | 20% | 2.5% | 40% | 30% |
| tebuconazole | 20% | 2.5% | 8% | 1.5% |
| ethylene glycol | 10% | 10% | 10% | 10% |
| nonylphenol polyethylene glycol ether (15 moles of ethylene oxide) | 6% | 1% | 5% | 7.5% |
| sodium lignosulfate | 10% | 5% | 9% | 11% |
| carboxymethylcellulose | 1% | 1% | 1% | 1% |
| 37% aqueous formaldehyde solution | 0.2% | 0.2% | 0.2% | 0.2% |
| silicone oil in the form of a 75% aqueous emulsion | 0.8% | 0.8% | 0.8% | 0.8% |
| water | 32% | 77% | 26% | 38% |

The active ingredients were intimately mixed with the adjuvants, giving a suspension concentrate from which suspension of any desired concentration could be obtained by dilution with water.

|  | e) | f) | g |
|---|---|---|---|
| propiconazole | 5% | 2.5% | 10% |
| tebuconazole | 5% | 2.5% | 5% |
| polyethylene glycol (MG 400) | 70% | — | — |
| N-methyl-2-pyrrolidone | 20% | — | — |
| epoxidised coconut oil | — | 1% | 1% |
| petroleum distillate (boiling range 160-190° C.) | — | 94% | 84% |

These solutions were suitable for application in the form of microdrops.

C. Biological examples

EXAMPLE 7

The synergistic activity of the mixtures or compositions of (I) and (II) according to the present invention can be demonstrated by comparing with the activity of the active ingredients (I) and (II) alone. The efficacy of the active ingredients against mycelial growth and sporulation of various fungi (Mucor, Rhizopus, Pythium) was determined in the poison plate assay. The required concentrations of the fungicide(s) were obtained by diluting the active ingredients (I), (II) or the combination of (I) and (II) dissolved in 50% aqueous ethanol with a calculated amount of sterile water and pouring said dilutions in Petri-dishes. Malt extract agar (3%) was added aseptically and uniform distribution was obtained by shaking. Each plate was inoculated with mycelium from the margin of an actively growing colony. After incubation at 22° C. and 70% relative humidity for a period long enough to allow complete growth of controls, diameters of colonies were measured. Relative activities were calculated by taking the absence of fungal growth (diameter 0 mm) as 100%. From the activity of the active ingredients alone, the expected activities E were calculated by using the so-called formula of Colby: (Colby, S. R. Weeds 1967, 15: 20–22), $$E = X + Y - \frac{X \cdot Y}{100}$$

wherein X and Y express the relative activities obtained for each of the active ingredients. A synergistic effect can be acknowledged if the found activity exceeds calculated activity.

The results are listed in the table 1 below and clearly demonstrate that the measured activity generally exceeds the calculated activity. Equal efficacy was observed whenever complete inhibition of fungal growth occured by one of the active ingredients (I) or (II) alone. The instances where an apparent antagonism occurred were caused by the deviant growth of the fungus where an active ingredient was tested alone.

TABLE 1

| Test-results in poison plate assay. | | | | |
|---|---|---|---|---|
| | | relative activity (%) | | |
| Active ingredient | Concentration ppm | MUCOR measured/ calculated | RHIZOPUS measured/ calculated | PYTHIUM measured/ calculated |
| Propiconazole (I) | 100 | 56 | 70 | 4 |
| | 50 | 4 | 0 | 8 |
| Tebuconazole (II) | 50 | 100 | 100 | 10 |
| | 20 | 56 | 66 | 0 |
| | 10 | 0 | 0 | 0 |
| | 5 | 0 | 0 | 0 |
| (I) + (II) | 100 + 50 | 100/100 | 100/100 | 70/14 |
| | 100 + 20 | 100/81 | 100/90 | 68/4 |
| | 100 + 10 | 98/56 | 100/70 | 26/4 |
| | 100 + 5 | 82/56 | 100/70 | 16/4 |
| | 50 + 50 | 100/100 | 100/100 | 50/17 |
| | 50 + 20 | 94/58 | 100/60 | 10/8 |
| | 50 + 10 | 32/4 | 92/0 | 0/8 |
| | 50 + 5 | 36/4 | 24/0 | 0/8 |
| Control distilled water/ ethanol | | 0 | 0 | 0 |

EXAMPLE 8

Wood rot test

The efficacy of mixtures of propiconazole (I) and tebuconazole (II) in preventing destruction of wood by fungi versus the efficacy of either active ingredient alone was tested in a mini soil block test with *Coniophora puteana* BAM 15 and *Gloeophyllum trabeum* BAM 109 as test fungi.

In the test formulations, the amount of the active ingredient propiconazole (I) was either 0.4% or 0.6% (w/w) and the amount of the active ingredient tebucanazole (II) was 0.2% (w/w). Test formulations further consisted of talloil ester 5% (w/w) and Kristalol 60 ® ad 100% (w/w).

For each test concentration, four unaged and four aged sapwood blocks of Pinus silvestris L. measuring $30 \times 10 \times 5$ mm were impregnated at retentions of 20 kg/m$^3$ and 40 kg/m$^3$ respectively. The ageing procedure consisted of heating the blocks at 80° C. for two weeks before impregnation. After impregnation both unaged and aged blocks were conditioned at 20° C. and 65% relative humidity for four weeks. After sterilization, the specimens were placed in glass jars with sterile soil and covered with two cm soil. Each jar contained two treated and two untreated specimens. The jars were inoculated with the test fungi and kept at 22° C. and 70% relative humidity for six weeks. The specimens were then dried and the weight losses calculated. A concentration was considered efficacious (+) when the mean weight loss of the four replicates was $\leq 3\%$. The results of the wood-rot test are shown in Table 2. The minus sign therein signifies that the mean weight loss due to fungal attack exceeded 3%.

| Active ingredient | Active ingredient content (% w/w) | | | | |
|---|---|---|---|---|---|
| Propiconazole (I) | 0.4 | 0.6 | — | 0.4 | 0.6 |
| Tebuconazole (II) | — | — | 0.2 | 0.2 | 0.2 |
| Retention kg/m$^3$ | Ageing | Weight loss: (+) $\leq$ 3% (−)> 3% | | | |
| *Coniophora puteana* BAM 15 | | | | | |
| 20 | — | + | + | − | + | + |
| | +80° C. | − | + | − | + | + |
| 40 | — | + | + | + | + | + |
| | +80° C. | + | + | − | + | + |
| *Gloeophyllum trabeum* BAM 109 | | | | | |
| 20 | — | − | − | − | + | + |
| | +80° C. | + | − | − | + | + |
| 40 | — | − | + | − | + | + |
| | +80° C. | − | − | − | + | + |

I claim:

1. A method of preserving wood or wood products which comprises treating the wood or wood products with an antifungally effective amount of an antifungal composition comprising (a) tebuconazole or a salt thereof, (b) propiconazole, a salt, a stereoisomer, or a stereoisomeric mixture thereof, and (c) a carrier, the proportion of the active ingredients (a) and (b) in said antifungal composition being such as to produce a synergistic antifungal effect, said proportion of the two active ingredients (a):(b) being within the range of from 1:1 to 1:50, by weight.

2. The method of claim 1 wherein the ratio by weight of the active ingredients (a):(b) is from 1:1 to 1:10.

3. The method of claim 1 wherein the ratio by weight of the active ingredients (a):(b) is 1:1.

4. The method of claim 1 wherein the ratio by weight of the active ingredients (a):(b) is from 1:1 to 1:5.

* * * * *